(12) United States Patent
Horii et al.

(10) Patent No.: US 9,562,859 B2
(45) Date of Patent: Feb. 7, 2017

(54) ANALYSIS DEVICE

(71) Applicant: FUJIFILM Corporation, Tokyo (JP)

(72) Inventors: Kazuyoshi Horii, Ashigarakami-gun (JP); Junpei Shiraishi, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 617 days.

(21) Appl. No.: 14/041,811

(22) Filed: Sep. 30, 2013

(65) Prior Publication Data

US 2014/0030151 A1    Jan. 30, 2014

Related U.S. Application Data

(63) Continuation of application No. PCT/JP2012/002186, filed on Mar. 29, 2012.

(30) Foreign Application Priority Data

Mar. 31, 2011  (JP) ................................. 2011-080908

(51) Int. Cl.
  *G01N 21/64* (2006.01)
  *G06F 1/20* (2006.01)
  (Continued)

(52) U.S. Cl.
  CPC ............. *G01N 21/6428* (2013.01); *B01L 7/00* (2013.01); *B01L 7/54* (2013.01); *G01N 21/0332* (2013.01);
  (Continued)

(58) Field of Classification Search
  CPC ..................... G06F 1/206; G01N 2035/00356; G01N 21/0332; G01N 21/648; G01N 21/6428; B01L 7/54; B01L 3/5027; B01L 7/00;B01L 2200/147; B01L 2300/0816; B01L 2300/1822; B01L 2300/1827; G05D 23/1931
  See application file for complete search history.

(56) References Cited

U.S. PATENT DOCUMENTS

| | | | |
|---|---|---|---|
| 6,194,223 B1 | 2/2001 | Herrmann et al. | |
| 2009/0185190 A1* | 7/2009 | Weinberger | B01L 7/00 356/450 |

(Continued)

FOREIGN PATENT DOCUMENTS

| | | | |
|---|---|---|---|
| JP | WO 2009-158304 A2 | 12/2009 | |
| JP | 2010-139332 A | 6/2010 | |

(Continued)

OTHER PUBLICATIONS

Extended European Search Report dated Sep. 2, 2014, issued in corresponding European Patent Application No. 12764665.1.

*Primary Examiner* — Shogo Sasaki
(74) *Attorney, Agent, or Firm* — Birch, Stewart, Kolasch & Birch, LLP

(57) ABSTRACT

An analysis device for performing analysis about a substance by using an analysis chip having therein a reaction area that reacts with the substance is provided. The analysis device includes: a control section in contact with the analysis chip; a first sensor for measuring an ambient temperature of the analysis chip; a second sensor for measuring the temperature at a contact area of the control section in contact with the analysis chip, and a control circuit for performing feedback control of the control section by finding a temperature of the contact area for achieving a desired temperature of the reaction area based on the ambient temperature measured by the first sensor and a temperature gradient between a position at which the ambient temperature is measured and the reaction area, setting the found tempera- (Continued)

ture as a target value and setting the temperature detected by the second sensor as an output value.

10 Claims, 2 Drawing Sheets

(51) Int. Cl.
*G01N 21/03* (2006.01)
*B01L 7/00* (2006.01)
*G05D 23/19* (2006.01)
*G01N 35/00* (2006.01)
*B01L 3/00* (2006.01)

(52) U.S. Cl.
CPC .......... *G05D 23/1931* (2013.01); *G06F 1/206* (2013.01); *B01L 3/5027* (2013.01); *B01L 2200/147* (2013.01); *B01L 2300/0816* (2013.01); *B01L 2300/1822* (2013.01); *B01L 2300/1827* (2013.01); *G01N 21/648* (2013.01); *G01N 2035/00356* (2013.01)

(56) References Cited

U.S. PATENT DOCUMENTS

| | | |
|---|---|---|
| 2009/0318306 A1 | 12/2009 | Hasson et al. |
| 2010/0279299 A1* | 11/2010 | Maltezos ............... B01L 7/52 435/6.11 |
| 2012/0176627 A1 | 7/2012 | Weinberger et al. |

FOREIGN PATENT DOCUMENTS

| | | |
|---|---|---|
| WO | WO 2009/072549 A1 | 6/2009 |
| WO | WO 2009/076372 A2 | 6/2009 |
| WO | WO 2010/115160 A2 | 10/2010 |

* cited by examiner

ANALYSIS DEVICE

CROSS-REFERENCE TO RELATED APPLICATIONS

This application is a Continuation of PCT International Application No. PCT/JP2012/002186 filed on Mar. 29, 2012, which claims priority to Patent Application No. 2011-080908 filed in Japan on Mar. 31, 2011, all of which are hereby expressly incorporated by reference into the present application.

TECHNICAL FIELD

The present invention relates to an analysis device for analyzing a substance to be detected contained in a sample liquid, or the like, and in particular to an analysis device for performing analysis using an analysis chip.

BACKGROUND ART

In various bio-measurements, the presence or absence and the amount of a substance to be detected, such as an antigen (or an antibody) is measured by detecting a biomolecular reaction, such as an antigen-antibody reaction. In this description, performing such a measurement, and determining a state, such as "positive" or "negative", based on a result of such a measurement are collectively referred to as "analysis".

For example, one of two substances that specifically bind to one another (such as an antigen, an antibody, an enzyme, a receptor, etc.) may be immobilized on a substrate, the other substance (which may be a substance to be detected, or a competing substance that competes with the substance to be detected in a sample) may be bound to the immobilized layer on the substrate, and the binding reaction may be detected to analyze the presence or absence and the amount of the substance to be detected in the sample.

Specifically, immunoassay is known, and examples thereof include: a sandwich method, which involves, in order to detect an antigen that is the substance to be detected contained in a sample, immobilizing an antibody that specifically binds to the antigen on a substrate, supplying the sample onto the substrate to have the antigen specifically bind to the antibody, adding a labeled antibody that specifically binds to the antigen and is provided with a label to have the labeled antibody bind to the antigen to form a so-called sandwich of antibody-antigen-labeled antibody, and detecting a signal from the label; and a competition method, which involves binding a labeled competing antigen to an immobilized antibody competitively with an antigen that is the substance to be detected, and detecting a signal from the label of the competing antigen that is bound to the immobilized antibody.

In the above-described sandwich method, the antigen that is the substance to be detected corresponds to "the other substance". In the competition method, the competing antigen corresponds to "the other substance". With the latter competition method, there is a relationship that a larger amount of the competing antigen bound to the immobilized antibody indicates a smaller amount of the antigen that is the substance to be detected, and therefore the amount of the antigen can be found from a level of the signal from the label, which corresponds to the amount of the competing antigen, based on the relationship.

Further, fluorescence detection methods are widely used as highly sensitive and simple measurement methods applicable to the above-described bio-measurements. In the fluorescence detection methods, a sample that is considered to contain a substance to be detected, which emits fluorescence when excited by light of a specific wavelength, is exposed to the excitation light of the specific wavelength, and the fluorescence emitted at that time is detected to check the presence of the substance to be detected. Further, in a case where the substance to be detected is not a fluorescent substance, it is widely practiced that a substance that specifically binds with the substance to be detected is labeled with a fluorescent colorant and is brought into contact with the sample, and then the fluorescence is detected in the same manner as described above to check the presence of the bond, i.e., the presence of the substance to be detected.

With respect to the above-described bio-analysis that uses optical techniques, reduction of a required time is desired, and various methods have been proposed for reducing a required time by efficiently causing a reaction at the reaction area. For example, U.S. Pat. No. 6,194,223 (hereinafter, Patent Document 1) proposes using an analysis chip having a microchannel and making a sample liquid flow down through the microchannel at a constant high speed, thereby speeding up the analysis. This type of analysis chip is also applicable to the above-described detection and quantitative analysis of a substance to be detected using the fluorescence detection.

In a case where the measurement as described above uses an immune reaction, an enzyme reaction, or the like, such reactions are highly temperature dependent, and therefore temperature control for accurately maintaining the reaction area at a predetermined temperature is performed during a measurement for diagnosis, etc., requiring high reliability. Japanese Unexamined Patent Publication No. 2010-139332 (hereinafter, Patent Document 2) discloses one example of an analysis device that involves such temperature control. To set the temperature of a reaction solution in a reaction vessel, which is the object of the temperature control, to a desired temperature, the device disclosed in Patent Document 2 measures the ambient temperature of the reaction vessel, in addition to the temperature of a constant temperature liquid forming a part of a temperature control means, and sets a target temperature of the constant temperature liquid depending on the ambient temperature to perform feedback control of the temperature of the constant temperature liquid based on the ambient temperature. Patent Document 2 also teaches heating the reaction solution with a heater, or the like, in place of the constant temperature liquid.

DISCLOSURE OF INVENTION

In a case where the temperature control of the reaction area is performed with respect to the above-described analysis device using an analysis chip, for example, there is a distance between the reaction area inside the chip and the bottom surface of the analysis chip in contact with a temperature control section including a heating or cooling means, such as a Peltier device, and this tends to cause a time delay in heat transfer from the temperature control section to the reaction area. In particular, in a case where a measurement optical system is positioned such that the excitation light travels below the reaction area of the analysis chip, the distance between the reaction area of the analysis chip and the bottom surface tends to be long to allow the excitation light to travel, and this often causes the above-described time delay in heat transfer. If there is a time delay in heat transfer, hunting of the temperature of the reaction area occurs, as shown in FIG. 4, when feedback control of the temperature control section is performed based on a measured temperature of the reaction area, and it is difficult to accurately control the temperature of the reaction area to a target temperature.

In the device disclosed in Patent Document 2, the control is performed with assuming that the temperature of the constant temperature liquid forming a part of the temperature control section is the same as the temperature of the reaction solution, which is the object of the temperature control, and it cannot address the problem of the hunting due to a delay in heat transfer between the reaction area and the temperature control section.

In view of the above-described circumstances, the present invention is directed to providing an analysis device for performing analysis using an analysis chip having a reaction area therein, wherein the temperature of the reaction area can be accurately set to a desired temperature without causing hunting.

An aspect of the analysis device according to the invention is an analysis device for performing analysis relating to a substance to be detected by using an analysis chip having therein a reaction area that reacts with the substance to be detected, the device including: a temperature control section in contact with the analysis chip; a first temperature sensor for measuring an ambient temperature of the analysis chip; a second temperature sensor for measuring a temperature at a contact area of the temperature control section in contact with the analysis chip; and a control circuit for performing feedback control of the temperature control section by finding a temperature of the contact area for achieving a desired temperature of the reaction area based on the ambient temperature measured by the first temperature sensor and a temperature gradient between a position at which the ambient temperature is measured and the reaction area, setting the found temperature as a target value and setting the temperature detected by the second temperature sensor as an output value.

The description "measuring an ambient temperature of the analysis chip" generally refers to measuring a temperature at a point that may be inside or outside the analysis device and is one of the points showing the temperature gradient, and includes measuring a temperature at a point spaced apart from the analysis chip or measuring a temperature at a point on the surface of the analysis chip.

The temperature control section may be a structure where a Peltier device, or the like, directly heats or cools the analysis chip, or a structure where such a device heats or cools the analysis chip via a heat-transfer member. In the case where the latter structure is employed, the second temperature sensor measures a temperature at a contact area of the heat-transfer member in contact with the analysis chip.

In the analysis device of the invention, it is desirable that the analysis chip is disposed such that the bottom surface thereof is in contact with the contact area of the temperature control section so as to have the same temperature as that of the contact area, the first temperature sensor is disposed at a position for detecting a temperature at a surface of the chip that is opposite from the bottom surface of the analysis chip, and a temperature T2 of the target value satisfies the equation below:

$$T2=\{1+(b/a)\}T\text{set}-(b/a)T1,$$

wherein a is a distance from the surface of the analysis chip to the reaction area, b is a distance from the bottom surface of the analysis chip to the reaction area, T1 is a temperature measured by the first temperature sensor, T2 is the temperature of the target value, and Tset is a desired temperature of the reaction area.

Further, it is desirable to apply the invention to an analysis device that includes a total reflection optical system having an optical path at a position between the reaction area of the analysis chip and the temperature control section, or an analysis device that includes a surface plasmon resonance optical system having an optical path at a position between the reaction area of the analysis chip and the temperature control section.

As described above, the analysis device of the invention includes a temperature control section in contact with the analysis chip, a first temperature sensor for measuring an ambient temperature of the analysis chip, a second temperature sensor for measuring a temperature at a contact area of the temperature control section in contact with the analysis chip, and a control circuit for performing feedback control of the temperature control section by finding a temperature of the contact area for achieving a desired temperature of the reaction area based on the ambient temperature measured by the first temperature sensor and a temperature gradient between a position at which the ambient temperature is measured and the reaction area, setting the found temperature as a target value and setting the temperature detected by the second temperature sensor as an output value (control value). Since the feedback control of the analysis device of the invention is not based on a measured temperature of the reaction area, no hunting of the temperature due to a time delay in heat transfer from the temperature control section to the reaction area occurs even when there is the time delay, thereby allowing accurately setting the temperature of the reaction area to a desired temperature.

In the case where the analysis device includes a total reflection optical system having an optical path of excitation light at a position between the reaction area of the analysis chip and the temperature control section or the analysis device includes a surface plasmon resonance optical system having an optical path at a position between the reaction area of the analysis chip and the temperature control section, the distance between the reaction area of the analysis chip and the bottom surface tend to be long, as mentioned above. Such a structure tends to have the above-described time delay in heat transfer, and therefore, if feedback control is performed based on a measured temperature at the reaction area, hunting of the temperature tends to occur. Therefore, it is particularly desirable to apply the invention to this type of analysis device in preventing the occurrence of hunting.

DESCRIPTION OF PREFERRED
EMBODIMENTS

Figure 1:
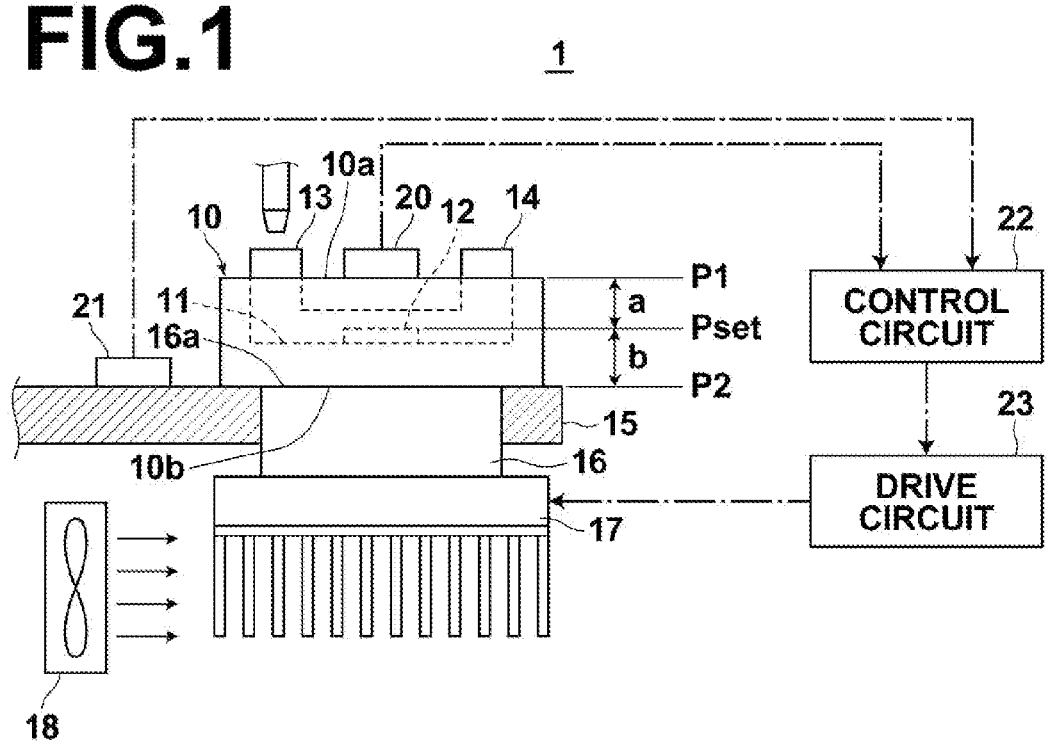
FIG. 1 is a schematic side view of an analysis device according to one embodiment of the present invention.
Figure 2:
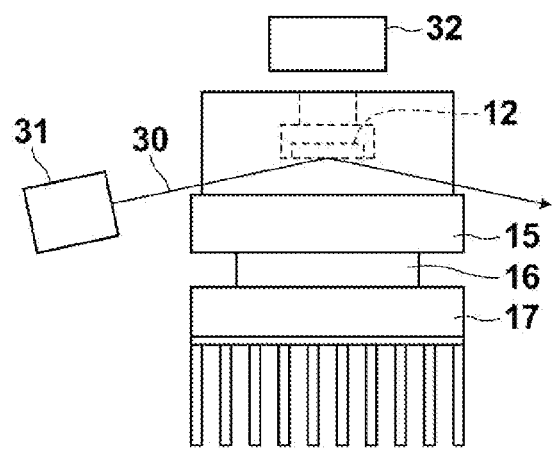
FIG. 2 is a front view of a part of the analysis device.

Hereinafter, an embodiment of the present invention will be described in detail with reference to the drawings. FIG. 1 shows a partially sectional side shape of an analysis device 1 according to one embodiment of the invention together with electric circuits thereof. FIG. 2 shoes the front shape of the main part of the analysis device.

The analysis device 1 of this embodiment detects, for example, a biologically derived substance by using a microchannel analysis chip (which will hereinafter simply be referred to as "analysis chip") 10 having a microchannel 11 therein. First, the analysis chip 10 is described. The analysis chip 10 is removably placed in the analysis device 1, and includes the microchannel 11 through which a sample liquid flows, a metal thin film 12 fixed on the bottom surface of the microchannel 11, a sample liquid inlet port 13 through which a sample liquid is introduced into the microchannel 11 via a nozzle, or the like, and a sample liquid outlet port 14 through which the sample liquid that has flown through the microchannel 11 is discharged out of the chip. It should be noted that, in place of the sample liquid inlet port 13, a reaction cup, or the like, where some reaction of the sample liquid is induced, may be provided, and the sample liquid may be introduced into the microchannel 11 from there.

On the surface of the metal thin film 12, one of two substances that specifically bind to one another, such as an antibody involved in an antigen-antibody reaction, is immobilized. The antibody may be directly immobilized on the wall surface of the microchannel 11. However, in this embodiment, the antibody is immobilized on the surface of the metal thin film 12 for enhancing fluorescence to be detected using an electric field enhancement effect due to surface plasmons, as described later. In this embodiment, the surface of the metal thin film 12 forms a reaction area where an antigen-antibody reaction is induced.

Next, the analysis device 1 is described. The analysis device 1 includes: a metal block 16 serving as a heat-transfer member made of, for example, aluminum and held by a base plate 15; a heating/cooling unit 17 formed, for example, by a Peltier device for heating or cooling the metal block 16; a fan 18 for cooling the heating/cooling unit 17; a first temperature sensor 20 for measuring the temperature of an upper surface 10a of the analysis chip 10 at a position above the metal thin film 12; a second temperature sensor 21 for measuring the temperature of an upper surface 16a (which forms a contact area in the invention) of the metal block 16 in contact with a bottom surface 10b of the analysis chip 10; a control circuit 22 to which temperature detection signals from the second temperature sensor 21 and the first temperature sensor 20 are inputted; and a drive circuit 23 that is controlled by the control circuit 22 to drive the heating/cooling unit 17.

In this embodiment, the metal block 16 and the heating/cooling unit 17 form a temperature control section in the invention.

Although not shown in FIG. 1, the analysis device 1 further includes, as shown in FIG. 2: a light source 31 formed by a semiconductor laser, or the like, for directing p-polarized excitation light 30 to the bottom surface (the interface between the channel wall and the metal thin film 12) of the microchannel 11 at an incidence angle that satisfies the total reflection condition; and an optical detector 32 for detecting fluorescence that is emitted from the upper portion of the metal thin film 12 of the analysis chip 10, as described later.

Next, detection and analysis of a substance to be detected performed using the analysis device 1 are described. As one example, a case of detection of an antigen that may possibly be contained in blood (whole blood), which is a sample liquid, is described. First, the whole blood is injected via the sample liquid inlet port 13 shown in FIG. 1, and a sample suction pump (not shown) connected to the sample liquid outlet port 14 is driven to introduce the whole blood into the microchannel 11 of the analysis chip 10.

The whole blood, which is the sample liquid, introduced into the microchannel 11 is mixed with a fluorescent label that is adsorptively immobilized on the microchannel 11 at a position upstream the metal thin film 12, for example. If the antigen to be analyzed is present in the whole blood, the fluorescent label binds with the antigen. When the whole blood flows above the metal thin film 12, the antigen (if any) in the whole blood binds with the antibody on the metal thin film 12.

The antigen thus adsorbed onto the metal thin film 12 is detected as follows. The excitation light 30 emitted from the light source 31 enters the bottom surface (the interface between the channel wall and the metal thin film 12) of the microchannel 11 at an incidence angle that satisfies the total reflection condition. When the excitation light 10 is totally reflected, evanescent light seeps from the bottom wall surface of the microchannel 11 into the sample liquid. At this time, if the antigen is present in a seeping area of the evanescent light, the fluorescent label bound to the antigen is excited to emit fluorescence. The thus generated fluorescence is detected by the optical detector 32. By detecting the presence of the fluorescent label in this manner, the presence of the antigen bound to the fluorescent label is detected. Thus, the presence or absence and the amount of the antigen can be detected based on a fluorescence detection signal from the optical detector 32.

Further, in particular, in this embodiment where the metal thin film 12 is formed, surface plasmons are excited in the metal thin film 12 by the evanescent light. The surface plasmons form an electric field distribution on the surface of the metal film, and thus an electric field enhanced area is formed. In the electric field enhanced area, the fluorescence is enhanced by the electric field enhancement effect, and this allows, in particular, highly sensitive detection of the presence or absence and the amount of the antigen.

Since the extent of the antigen-antibody reaction is temperature dependent, it is required to control the temperature at the surface of the metal thin film 12, which is the reaction area, to a desired constant value in order to obtain a reproducible result of the analysis. To this end, in this embodiment, the control circuit 22, which receives the temperature detection signals from the first temperature sensor 20 and the second temperature sensor 21, finds a temperature of the upper surface 16a of the metal block for achieving the desired temperature of the surface of the metal thin film 12 based on the temperature (ambient temperature) of the upper surface 10a of the analysis chip 10 measured by the first temperature sensor 20 and a temperature gradient between the upper surface 10a and the surface of the metal thin film 12. Then, the control circuit 22 sets the found temperature as a target value and sets the temperature at the upper surface 16a of the metal block detected by the second temperature sensor 21 as an output value (control value) to perform feedback control of the operation of the drive circuit 23, that is, the operation of the heating/cooling unit 17. In this manner, the temperature at the surface of the metal thin film 12 is maintained at the desired temperature.

Figure 3:
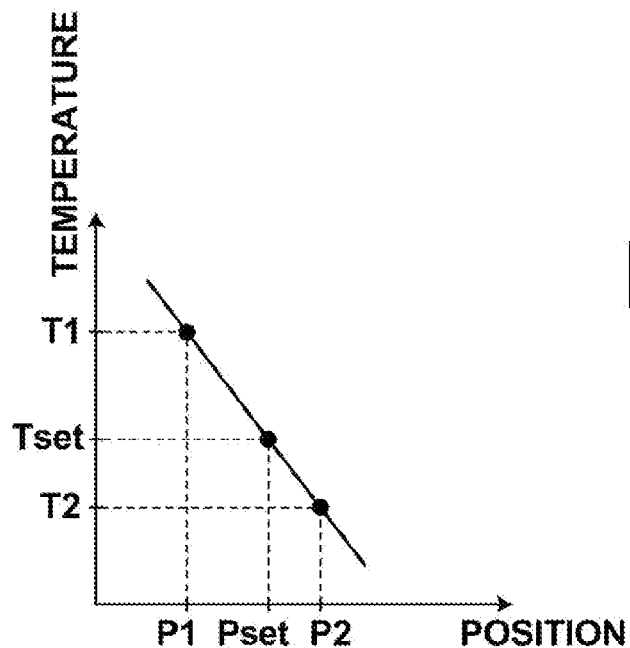
FIG. 3 is a diagram for explaining temperature settings of a reaction area in the analysis device.
Figure 4:
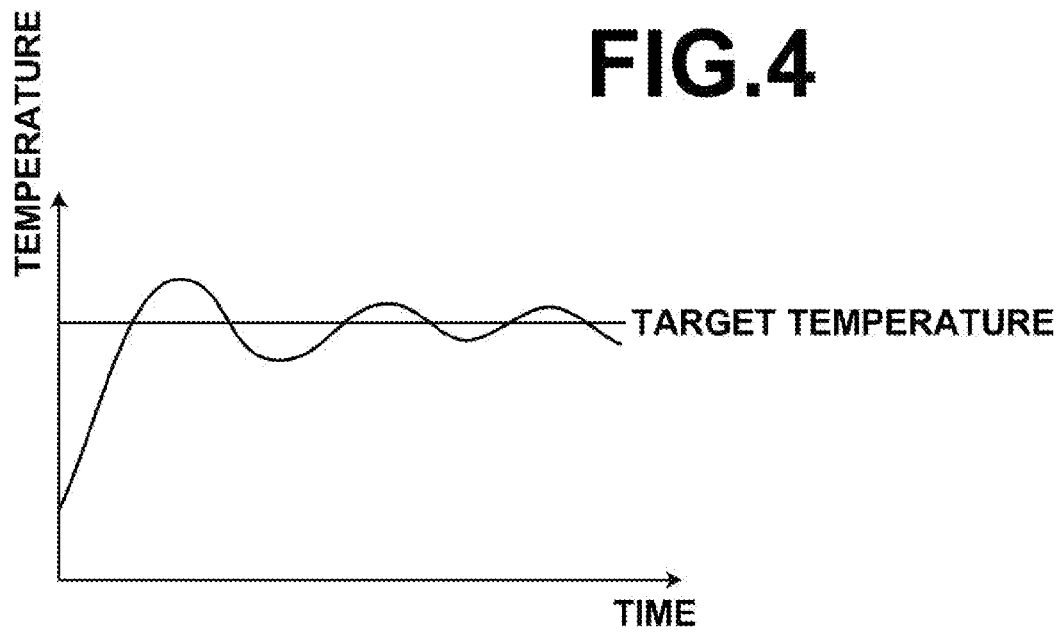
FIG. 4 is a diagram for explaining hunting of a temperature of an analysis section that occurs with a conventional device.

The target value is determined by the control circuit 22 as follows. FIG. 3 shows a relationship between the temperature measurement position and the temperature in the structure shown in FIGS. 1 and 2. The straight line shown in FIG. 3 represents a temperature gradient between a temperature measurement position P1 of the first temperature sensor 20 and a surface position Pset of the metal thin film 12, which is the object of the temperature control to set the desired temperature. Such a temperature gradient can be found in advance by experiments, or the like, for each of several assumed combinations of a temperature T1 at the temperature measurement position P1 and a desired temperature Tset at the position Pset. The control circuit 22 stores the thus found temperature gradient characteristics in an internal memory.

Then, the control circuit 22 extrapolates the relationship between the temperature T1 at the position P1 and the desired temperature Tset at the position Pset, as shown in FIG. 3, to find a temperature T2 at the temperature measurement position of the second temperature sensor 21, i.e., at the upper surface 16a of the metal block. The temperature T2 is the target value of the feedback control. By controlling the temperature of the upper surface 16a of the metal block to the temperature T2, the temperature of the surface of the metal thin film 12 is set the desired temperature Tset.

More specifically, assuming that "a" is a distance from the upper surface 10a of the analysis chip 10 to the surface of the metal thin film 12 and "b" is a distance from the surface of the metal thin film 12 to the bottom surface 10b of the analysis chip 10, the temperature T2 is calculated as follows:

$$T2=\{1+(b/a)\}Tset-(b/a)T1$$

It is apparent from the relationship among the three points shown in FIG. 3 that the thus calculated temperature T2 is an appropriate temperature. As one example, the distances a and b are about 2 mm and 3 mm, respectively. Further, in general, the depth of the microchannel 11 is several micrometers to several millimeters. The temperature of the sample liquid is often uniform across the entire range of the depth, and therefore the reaction area in the invention can be set at an arbitrary depth position in the entire range of the depth.

Now, a temperature control formula for finding the temperature T2 by extrapolation is explained. In the following description, a case where an ambient temperature at one point is found and a case where ambient temperatures at two points are found are explained, where the ambient temperature in the former case is represented by Tenv, and the ambient temperatures in the latter case are represented by Tenv1 and Tenv2.

First, in the case where the ambient temperature at one point is found, the following two formulae are conceivable as the temperature control formula, where all the "k"s with a numeral are constants.

$$Tset = k_1 Tenv + k_2 \quad (1)$$

$$Tset = k_3 Tenv^2 + k_4 Tenv + k_5 \quad (2)$$

Next, in the case where the ambient temperatures at two points are found, the following two formulae are conceivable as the temperature control formula.

$$Tset = k_1 Tenv1 + k_2 Tenv2 + k_3 \quad (3)$$

$$Tset = k_4 Tenv1^2 + k_5 Tenv2^2 + k_6 Tenv1 Tenv2 + k_7 Tenv1 + k_8 Tenv2 + k_9 \quad (4)$$

As described above, the temperature control of this embodiment is not performed based on a measured temperature at the surface of the metal thin film 12, which is the object of the temperature control. Therefore, even when there is a time delay in heat transfer between the upper surface 16a of the metal block and the surface of the metal thin film 12, hunting of the temperature of the surface of the metal thin film 12 does not occur.

Further, in this embodiment, in particular, a surface plasmon resonance optical system having an optical path of the excitation light 30 at a position between the metal thin film 12 and the metal block 16 is provided, and therefore the distance between the bottom surface 10b of the analysis chip 10 and the surface of the metal thin film 12 tends to be long to allow the optical path to extend therebetween. Namely, as one example, this distance usually needs to be 100 μm or more, and, in order to facilitate setting the optical path, the distance may preferably be 1 mm or more, or more preferably be 3 mm or more.

Thus, this structure intrinsically tends to have a time delay in heat transfer, and therefore if feedback control is performed based on a measured temperature at the surface of the metal thin film 12, hunting of the temperature tends to occur. This embodiment, where the invention is applied to this type of structure, is particularly desirable in preventing the occurrence of hunting.

It should be noted that, in place of providing the metal thin film 12 and using an optical system for generating surface plasmon resonance as in this embodiment, the detection and analysis of a substance to be detected may be achieved using an optical system where light is totally reflected at the bottom wall surface of the microchannel 11 to have the bottom wall surface generate evanescent light with utilizing the fact that the amount of total reflection light attenuates when the substance to be detected adheres to the bottom wall surface. Also in this case, the distance between the bottom surface 10b of the analysis chip 10 and the bottom wall surface of the microchannel 11 tends to be long due to the presence of the optical path. Therefore, it is also particularly desirable to apply the invention to an analysis device having the above-mentioned structure in preventing the occurrence of hunting.

Although the temperature at the upper surface 10a of the analysis chip 10 is measured as the ambient temperature by the first temperature sensor 20 in the above-described embodiment, a temperature at a point in the atmosphere above the upper surface 10a of the analysis chip may be measured as the ambient temperature. Also in this case, the temperature T2 for setting the temperature of the reaction area, such as the surface of the metal thin film 12, to the desired temperature Tset can be appropriately found based on the relationship shown in FIG. 3.

Further, the invention is similarly applicable to an analysis device that uses an analysis chip including the previously-mentioned reaction cup, where a primary reaction is induced in the reaction cup as pre-processing, and then a secondary reaction is induced in the channel in the chip. In this case, the area where the secondary reaction is induced is the reaction area, and the temperature control may be performed to set the temperature of the area to a desired temperature.

What is claimed is:

1. An analysis device configured to perform analysis relating to a substance to be detected, the device comprising:
   an analysis chip having therein a reaction area that reacts with the substance to be detected at a predetermined temperature;
   a temperature control section comprising a heat-transfer member which has a contact area in contact with the analysis chip and is configured to heat or cool the analysis chip to the predetermined temperature via the heat-transfer member;
   a first temperature sensor configured to measure an ambient temperature at a measurement area of a surface of the analysis chip, wherein the measurement area is different from the contact area;
   a second temperature sensor configured to measure a contact area temperature at the contact area; and a control circuit comprising an inner memory storing a temperature gradient between the temperature of the measurement area and the temperature of the reaction area; and a drive circuit configured to receive control signals from the control unit to drive the temperature control section, wherein the control circuit is configured to perform feedback control of the temperature control section by receiving a signal representing the contact area temperature and a signal representing the ambient area temperature, calculating a target temperature at the contact area so as to make the reaction area be the predetermined temperature based on the temperature gradient read from the inner memory and the ambient temperature, and sending the control signals according to the calculated target temperature to the drive circuit such that the contact area temperature of the contact area is closer to the target temperature; wherein the analysis chip is disposed such that the bottom surface thereof is in contact with the contact area of the temperature control section so as to have the same temperature as that of the contact area, and wherein the measurement area is included in an opposite surface of the analysis chip from the bottom surface of the analysis chip, wherein the target temperature T2 satisfies the equation below:

$$T2=\{1+(b/a)\}T\text{set}-(b/a)T1, \text{ and}$$

wherein a is a distance from the opposite surface to the reaction area, b is a distance from the bottom surface to the reaction area, T1 is the ambient temperature, T2 is the target temperature, and Tset is the predetermined temperature of the reaction area.

2. The analysis device as claimed in claim 1, wherein the temperature control section comprises a heat-transfer member in contact with the analysis chip and heats or cools the analysis chip via the heat-transfer member, and the second temperature sensor measures a temperature at a contact area of the heat-transfer member in contact with the analysis chip.

3. The analysis device as claimed in claim 1, further comprising a total reflection optical system having an optical path at a position between the reaction area of the analysis chip and the temperature control section.

4. The analysis device as claimed claim 2, further comprising a total reflection optical system having an optical path at a position between the reaction area of the analysis chip and the temperature control section.

5. The analysis device as claimed in claim 1, further comprising a light source configured to provide the reaction area with an excitation light to produce a surface plasmon resonance on the reaction area, which is a metal thin film.

6. The analysis device as claimed in claim 2, further comprising a light source configured to provide the reaction area with an excitation light to produce a surface plasmon resonance on the reaction area, which is a metal thin film.

7. The analysis device as claimed in claim 1, wherein the analysis chip is disposed such that a bottom surface thereof contacts the contact area of the temperature control section so as to have the same temperature as that of the contact area, and wherein the measurement area is included in a top surface of the analysis chip.

8. The analysis device as claimed in claim 1, further comprising an optical detector configured to detect light at the reaction area and to send a detection signal to the control circuit.

9. The analysis device as claimed in claim 8, wherein the control circuit is configured to analyze the detection signal from the optical detector and to perform at least one of specifying the presence or absence of and specifying the amount of the substance to be detected.

10. The analysis device as claimed in claim 1, wherein a binding substance, which binds with the substance to be detected at a predetermined temperature, is immobilized at the reaction area.

\* \* \* \* \*